US009224124B2

(12) United States Patent
Rahim et al.

(10) Patent No.: US 9,224,124 B2
(45) Date of Patent: Dec. 29, 2015

(54) ITEM STORAGE AND TRACKING CABINET AND ARRANGEMENT

(71) Applicant: Mobile Aspects, Inc., Pittsburgh, PA (US)

(72) Inventors: Muhammad R. Rahim, Monroeville, PA (US); Khang Nguyen Le, Murrieta, CA (US); Timur P. Sriharto, Monroeville, PA (US); Pribadi Kardono, Monroeville, PA (US); Suneil Mandava, Pittsburgh, PA (US)

(73) Assignee: Mobile Aspects, Inc., Pittsburgh, PA (US)

( * ) Notice: Subject to any disclaimer, the term of this patent is extended or adjusted under 35 U.S.C. 154(b) by 0 days.

(21) Appl. No.: 14/524,542

(22) Filed: Oct. 27, 2014

(65) Prior Publication Data

US 2015/0115029 A1 Apr. 30, 2015

Related U.S. Application Data

(60) Provisional application No. 61/896,828, filed on Oct. 29, 2013.

(51) Int. Cl.
*G06F 19/00* (2011.01)
*G06Q 30/00* (2012.01)
*G06Q 90/00* (2006.01)
*G06Q 10/08* (2012.01)

(52) U.S. Cl.
CPC .................................. *G06Q 10/087* (2013.01)

(58) Field of Classification Search
USPC ........ 235/375, 383, 385, 381; 340/10.1, 10.2, 340/572.1
See application file for complete search history.

(56) References Cited

U.S. PATENT DOCUMENTS

| 3,958,102 A | 5/1976 | Burt |
| 4,116,512 A | 9/1978 | Wiser |
| 4,118,693 A | 10/1978 | Novikoff |
| 4,227,037 A | 10/1980 | Layton |
| 4,496,406 A | 1/1985 | Dedow |

(Continued)

FOREIGN PATENT DOCUMENTS

| JP | 2001052054 A | 2/2001 |
| JP | 2002282200 A | 10/2002 |

OTHER PUBLICATIONS

U.S. Appl. No. 14/013,625, filed Aug. 29, 2013.

(Continued)

*Primary Examiner* — Tuyen K Vo
(74) *Attorney, Agent, or Firm* — The Webb Law Firm

(57) ABSTRACT

An item storage and tracking unit for holding a plurality of discrete items may include a housing including a plurality of receptacles positioned therein and defining a plurality of associated inner areas. A signal emitting device is associated with at least one item and configured to emit a signal. At least one movement sensor and/or at least one weight sensor may be associated with each receptacle of the plurality of receptacles. At least one signal receiving arrangement is associated with each receptacle and configured to scan at least a portion of the inner area of the associated receptacle for the signal emitted from the signal emitting device associated with the at least one item. The scan is initiated at least partly in response to a determination by the at least one movement sensor, the at least one weight sensor, and/or an antenna associated with the associated receptacle.

18 Claims, 7 Drawing Sheets

(56) References Cited

U.S. PATENT DOCUMENTS

| | | | |
|---|---|---|---|
| 4,636,634 A | 1/1987 | Harper et al. |
| 4,636,950 A | 1/1987 | Caswell et al. |
| 4,673,932 A | 6/1987 | Ekchian et al. |
| 4,847,764 A | 7/1989 | Halvorson |
| 4,860,918 A | 8/1989 | Wuyten et al. |
| 5,029,183 A | 7/1991 | Tymes |
| 5,194,856 A | 3/1993 | Zijlstra |
| 5,287,414 A | 2/1994 | Foster |
| 5,295,154 A | 3/1994 | Meier et al. |
| 5,389,919 A | 2/1995 | Warren et al. |
| 5,408,443 A | 4/1995 | Weinberger |
| 5,410,315 A | 4/1995 | Huber |
| 5,413,236 A | 5/1995 | Kenevan |
| 5,431,299 A | 7/1995 | Brewer et al. |
| 5,495,961 A | 3/1996 | Maestre |
| 5,565,858 A | 10/1996 | Guthrie |
| 5,689,238 A | 11/1997 | Cannon, Jr. et al. |
| 5,713,485 A | 2/1998 | Liff et al. |
| 5,729,697 A | 3/1998 | Schkolnick et al. |
| 5,739,765 A | 4/1998 | Stanfield et al. |
| 5,751,220 A | 5/1998 | Ghaffari |
| 5,751,221 A | 5/1998 | Stanfield et al. |
| 5,765,707 A | 6/1998 | Kenevan |
| 5,771,003 A | 6/1998 | Seymour |
| 5,774,053 A | 6/1998 | Porter |
| 5,774,059 A | 6/1998 | Henry et al. |
| 5,797,515 A | 8/1998 | Liff et al. |
| 5,801,628 A | 9/1998 | Maloney |
| 5,804,810 A | 9/1998 | Woolley et al. |
| 5,857,152 A | 1/1999 | Everett |
| 5,912,818 A | 6/1999 | McGrady et al. |
| 5,917,433 A | 6/1999 | Keillor et al. |
| 5,936,527 A | 8/1999 | Isaacman et al. |
| 5,950,630 A | 9/1999 | Portwood et al. |
| 5,993,046 A | 11/1999 | McGrady et al. |
| 6,075,441 A | 6/2000 | Maloney |
| 6,112,502 A | 9/2000 | Frederick et al. |
| 6,116,461 A | 9/2000 | Broadfield et al. |
| 6,127,928 A | 10/2000 | Issacman et al. |
| 6,204,764 B1 | 3/2001 | Maloney |
| 6,296,148 B1 | 10/2001 | Myers et al. |
| 6,323,782 B1 | 11/2001 | Stephens et al. |
| 6,392,544 B1 | 5/2002 | Collins |
| 6,407,665 B2 | 6/2002 | Maloney |
| 6,424,262 B2 | 7/2002 | Garber et al. |
| 6,445,297 B1 | 9/2002 | Nicholson |
| 6,512,459 B2 | 1/2003 | Benezech et al. |
| 6,512,478 B1 | 1/2003 | Chien |
| 6,677,857 B2 | 1/2004 | Bara et al. |
| 6,703,935 B1 | 3/2004 | Chung et al. |
| 6,707,381 B1 | 3/2004 | Maloney |
| 6,714,121 B1 | 3/2004 | Moore |
| 6,718,888 B2 | 4/2004 | Muirhead |
| 6,745,027 B2 | 6/2004 | Twitchell, Jr. |
| 6,747,558 B1 | 6/2004 | Thorne et al. |
| 6,750,771 B1 | 6/2004 | Brand |
| 6,762,676 B2 | 7/2004 | Teowee et al. |
| 6,826,514 B1 | 11/2004 | Antico et al. |
| 6,870,464 B2 | 3/2005 | Okamura |
| 6,943,678 B2 | 9/2005 | Muirhead |
| 6,989,749 B2 | 1/2006 | Mohr |
| 7,009,518 B2 | 3/2006 | Liao et al. |
| 7,009,576 B2 | 3/2006 | Adamson et al. |
| 7,126,926 B1 | 10/2006 | Bjorklund et al. |
| 7,130,773 B1 | 10/2006 | Wong |
| 7,135,973 B2 | 11/2006 | Kittel et al. |
| 7,152,791 B2 | 12/2006 | Chappidi et al. |
| 7,187,287 B2 | 3/2007 | Ryal |
| 7,233,620 B2 | 6/2007 | Brommer |
| 7,256,682 B2 | 8/2007 | Sweeney, II |
| 7,265,675 B1 | 9/2007 | Carrender et al. |
| 7,286,043 B2 | 10/2007 | Carrender et al. |
| 7,298,243 B2 | 11/2007 | Juels et al. |
| 7,310,045 B2 | 12/2007 | Inui |
| 7,318,261 B2 | 1/2008 | Bills |
| 7,342,496 B2 | 3/2008 | Muirhead |
| 7,348,884 B2 | 3/2008 | Higham |
| 7,401,375 B2 | 7/2008 | McLeod |
| 7,420,458 B1 | 9/2008 | Kuzma et al. |
| 7,433,648 B2 | 10/2008 | Bridgelall |
| 7,758,523 B2 | 7/2010 | Collings et al. |
| 8,120,497 B2 | 2/2012 | Binmore |
| 8,484,049 B2 | 7/2013 | Mullenger et al. |
| 2001/0002448 A1 | 5/2001 | Wilson et al. |
| 2001/0028308 A1 | 10/2001 | De La Huerga |
| 2001/0034613 A1 | 10/2001 | Rubsamen |
| 2001/0044731 A1 | 11/2001 | Coffman et al. |
| 2001/0052054 A1 | 12/2001 | Franke et al. |
| 2002/0027507 A1 | 3/2002 | Yarin et al. |
| 2002/0038167 A1 | 3/2002 | Chirnomas |
| 2002/0063622 A1 | 5/2002 | Armstrong et al. |
| 2002/0113082 A1 | 8/2002 | Leatherman et al. |
| 2002/0143320 A1 | 10/2002 | Levin |
| 2002/0145520 A1 | 10/2002 | Maloney |
| 2002/0153411 A1 | 10/2002 | Wan et al. |
| 2002/0183882 A1 | 12/2002 | Dearing et al. |
| 2002/0190871 A1 | 12/2002 | Stanfield et al. |
| 2003/0030539 A1 | 2/2003 | McGarry et al. |
| 2003/0034390 A1 | 2/2003 | Linton et al. |
| 2003/0117281 A1* | 6/2003 | Sriharto et al. ............ 340/568.1 |
| 2003/0160698 A1 | 8/2003 | Andreasson et al. |
| 2003/0164401 A1 | 9/2003 | Andreasson et al. |
| 2003/0174099 A1 | 9/2003 | Bauer et al. |
| 2004/0046020 A1 | 3/2004 | Andreasson et al. |
| 2004/0069850 A1 | 4/2004 | De Wilde |
| 2004/0069852 A1 | 4/2004 | Seppinen et al. |
| 2004/0111335 A1 | 6/2004 | Black et al. |
| 2004/0155003 A1 | 8/2004 | Anderson et al. |
| 2004/0168618 A1 | 9/2004 | Muirhead |
| 2004/0178269 A1* | 9/2004 | Pradhan et al. .......... 235/462.13 |
| 2004/0267545 A1 | 12/2004 | Buchmann et al. |
| 2005/0024211 A1 | 2/2005 | Maloney |
| 2005/0088284 A1 | 4/2005 | Zai et al. |
| 2005/0088305 A1 | 4/2005 | Greene et al. |
| 2005/0093679 A1 | 5/2005 | Zai et al. |
| 2005/0099283 A1 | 5/2005 | Johnson et al. |
| 2005/0237184 A1 | 10/2005 | Muirhead |
| 2005/0241548 A1 | 11/2005 | Muirhead |
| 2005/0280539 A1 | 12/2005 | Pettus |
| 2006/0022800 A1 | 2/2006 | Krishna et al. |
| 2006/0028081 A1 | 2/2006 | Minagawa |
| 2006/0056370 A1 | 3/2006 | Hancock et al. |
| 2006/0058018 A1 | 3/2006 | Toulis et al. |
| 2006/0092040 A1 | 5/2006 | Fishkin et al. |
| 2006/0109084 A1 | 5/2006 | Yarvis |
| 2006/0143439 A1 | 6/2006 | Arumugam et al. |
| 2006/0187043 A1 | 8/2006 | Allen |
| 2006/0215593 A1 | 9/2006 | Wang et al. |
| 2007/0046467 A1 | 3/2007 | Chakraborty et al. |
| 2007/0096876 A1 | 5/2007 | Bridgelall et al. |
| 2007/0103303 A1 | 5/2007 | Shoarinejad |
| 2007/0164109 A1 | 7/2007 | Ridings et al. |
| 2007/0171992 A1 | 7/2007 | Shameli et al. |
| 2007/0172007 A1 | 7/2007 | Shoarinejad et al. |
| 2007/0188342 A1 | 8/2007 | Valeriano et al. |
| 2007/0200724 A1 | 8/2007 | Lazo et al. |
| 2007/0216534 A1 | 9/2007 | Ferguson et al. |
| 2007/0279202 A1 | 12/2007 | Lionetti |
| 2008/0052037 A1* | 2/2008 | Bodin et al. .................. 702/173 |
| 2008/0055084 A1* | 3/2008 | Bodin et al. ............... 340/572.1 |
| 2008/0061940 A1 | 3/2008 | Onderko et al. |
| 2008/0117050 A1 | 5/2008 | Wu et al. |
| 2008/0198016 A1 | 8/2008 | Lawrence et al. |

(56) References Cited

U.S. PATENT DOCUMENTS

| | | | |
|---|---|---|---|
| 2008/0218354 | A1 | 9/2008 | Lorentz et al. |
| 2009/0009332 | A1 | 1/2009 | Nunez et al. |
| 2009/0138303 | A1* | 5/2009 | Seshadri .......................... 705/7 |
| 2009/0261956 | A1 | 10/2009 | Ojeda et al. |
| 2011/0153614 | A1* | 6/2011 | Solomon ..................... 707/740 |
| 2014/0316561 | A1* | 10/2014 | Tkachenko ........... G07F 11/002 700/236 |

OTHER PUBLICATIONS

U.S. Appl. No. 14/487,809, filed Sep. 16, 2014.

U.S. Appl. No. 14/455,131, filed Aug. 8, 2014.

U.S. Appl. No. 14/558,064, filed Dec. 2, 2014.

U.S. Appl. No. 13/662,897, filed Oct. 29, 2012.

U.S. Appl. No. 13/793,201, filed Mar. 11, 2013.

\* cited by examiner

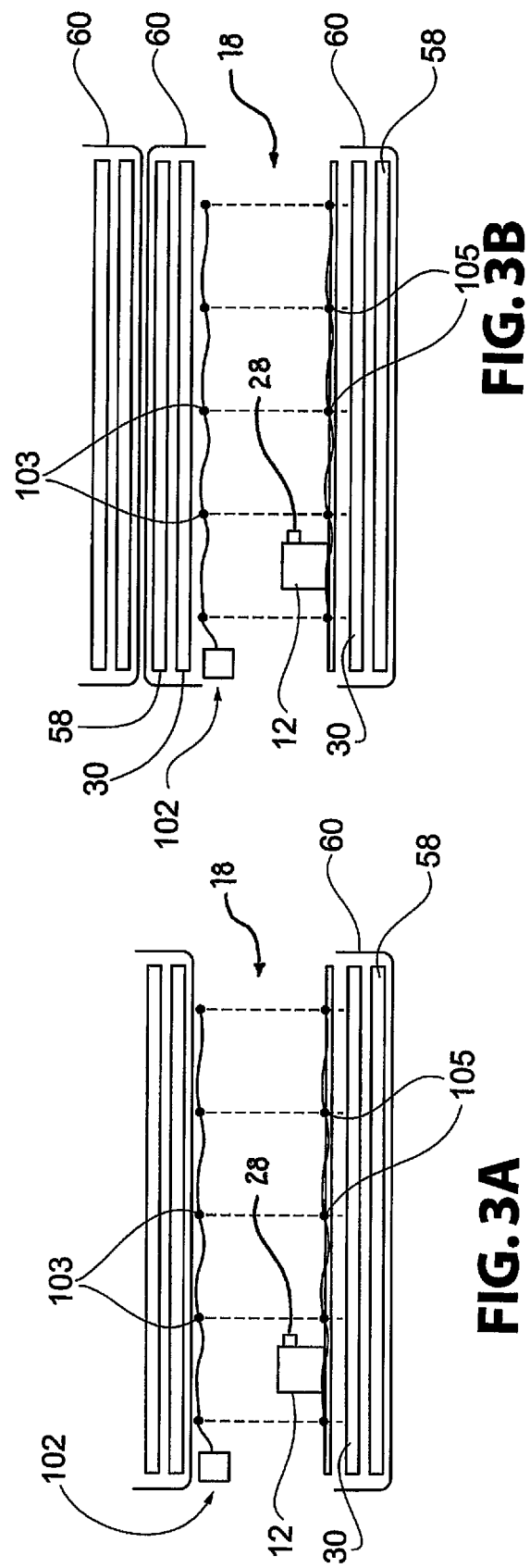

ITEM STORAGE AND TRACKING CABINET AND ARRANGEMENT

CROSS REFERENCE TO RELATED APPLICATIONS

This application claims the benefit of priority to U.S. Provisional Application No. 61/896,828 filed on Oct. 29, 2013, the entire contents of which are incorporated herein by reference.

BACKGROUND OF THE INVENTION

1. Field of the Invention

Preferred and non-limiting embodiments or aspects are related to an item storage and tracking cabinet and arrangement containing multiple and discrete items and, in particular, to an item storage and tracking cabinet and arrangement for securely tracking items with improved efficiency.

2. Description of Related Art

In many industrial and service applications, multiple items must be tracked for a variety of reasons. For example, these items may be tracked so that the user knows when additional items should be obtained or ordered, who is using the items and for what purpose, and for expensive items, a secure tracking system is required. Whether for security purposes or inventory purposes, an identification system can be developed in order to accurately track and manage a large amount of items, typically discrete and small items.

Health care delivery institutions, like hospitals, have a large amount of inventory to control throughout their system. Thousands of items move in and out of supply and operating rooms every day, and the system administrators would like to know exactly what items are being used, when they are being used, who is using them, and how often. At all times, it is preferable that all items be accounted for, and be stocked to an acceptable level.

In order to more effectively track items, supply cabinets have been developed, which provide inventory, accountability, and security of supplies, e.g., medical supplies. Some conventional art cabinets utilize manual input systems. To gain access to a cabinet, the user must input, on a keyboard, their access information, such as a PIN. A door to the cabinet is unlocked after the internal computer accepts the access information. The supply items are separated into bins, by type, and as a user takes out an item, they push a button, indicating that they have taken out that item. This action of manual input causes the system to decrement the item from inventory.

RFID-based supply cabinets have also been developed to more effectively track items. Conventional RFID-based supply cabinets for tracking items identify an RFID tag on each item by scanning each shelf in a cabinet in response to a door open/close event. The cabinet may contain one or more shelves. Based on conventional scanning technology, a time to scan each shelf in the cabinet may vary from 4 seconds to 20 seconds, depending on the type of items. For example, a time required to scan an eight-shelf cabinet is at least 32 seconds, i.e., 8 shelves multiplied by 4 seconds for each shelf. During scanning, the door to the cabinet must be locked, and the entire cabinet is unavailable to users. Usability of cabinets in high-traffic areas is problematic when scanning times are too long; for example, if a cabinet cluster contains 8 cabinets with each cabinet containing 8 shelves. However, reducing scanning time to less than 4 seconds per shelf using conventional scanning technology significantly reduces scanning accuracy. Accordingly, conventional storage, tracking, and inventory management systems are ineffective and/or inefficient in monitoring and tracking items stored therein.

SUMMARY OF THE INVENTION

Generally, provided is an improved item storage and tracking cabinet and arrangement. Preferably, provided is an item storage and tracking cabinet and arrangement that provides a reduced scanning time, while maintaining scanning accuracy. Preferably, provided is an item storage and tracking cabinet and arrangement that avoids unnecessary scanning time. Preferably, provided is an item storage and tracking cabinet and arrangement that provides reliable shielding between shelves to improve scanning accuracy.

According to a preferred and non-limiting embodiment or aspect, an item storage and tracking unit for holding a plurality of discrete items may include a housing including a plurality of receptacles positioned therein and defining a plurality of associated inner areas. At least one signal emitting device is associated with at least one item of the plurality of discrete items and configured to emit a signal. The at least one item is accessible by accessing at least one receptacle of the plurality of receptacles. At least one movement sensor is associated with each receptacle of the plurality of receptacles and configured to detect access to the at least one receptacle. At least one signal receiving arrangement is associated with each receptacle of the plurality of receptacles and configured to scan at least a portion of the inner area of the associated receptacle for the signal emitted from the at least one signal emitting device associated with the at least one item of the plurality of discrete items. The scan is initiated at least partly in response to the at least one movement sensor associated with the associated receptacle detecting access to the associated receptacle.

The signal may include a characteristic unique to the at least one item and/or a category or type of item. At least one of the plurality of items may be positionable within at least one of the inner areas in any position and/or orientation. The at least one signal emitting device may include at least one radio frequency transponder, and the at least one signal receiving arrangement may include at least one antenna. The at least one signal receiving arrangement may be configured to not initiate a scan of the inner area of the associated receptacle for the signal emitted from the at least one signal emitting device if the at least one movement sensor associated with the associated receptacle does not detect access to the associated receptacle.

The item storage and tracking unit may further include at least one weight sensor associated with each receptacle of the plurality of receptacles and configured to measure a weight before the at least one movement sensor associated with the associated receptacle detects an access to or interaction with the associated receptacle, and a weight after the at least one movement sensor associated with the associated receptacle detects an access to or interaction with the associated receptacle. The at least one signal receiving arrangement may be configured to scan the inner area of the associated receptacle if the weight before the detected access is different from the weight after the detected access. The at least one signal receiving arrangement may be configured to not initiate a scan of the inner area of the associated receptacle if the weight before the detected access is substantially equal to the weight after the detected access. The measured weight may include the weight of at least one of the following: a portion of the structure defining the inner area, a portion of the receptacle, a surface of the receptacle, at least one item of the plurality of items, or any combination thereof.

The item storage and tracking unit may further include at least one controller (control device, and/or computer) configured to directly or indirectly communicate with and/or control at least one of the following: the at least one signal emitting device, the at least one signal receiving arrangement, the at least one movement sensor, at least one weight sensor, at least one lock mechanism, at least one computer associated with the unit, at least one display associated with the unit, at least one interface associated with the unit, at least one input device associated with the unit, at least one component of the unit, or any combination thereof.

The at least one surface or area of the unit may include at least one shielding element configured to minimize, redirect, and/or prevent the signal emitted from the at least one signal emitting device from passing therethrough. The at least one surface defining the inner area of the associated receptacle may include at least one shielding element. The item storage and tracking unit may further include at least one absorption layer between the at least one signal receiving arrangement and the at least one shielding element. The at least one shielding element may include at least one substantially U-shaped shielding element. The item storage and tracking unit may further include at least one absorption layer between the at least one signal receiving arrangement and the at least one U-shaped shielding element, wherein a substantially U-shaped field extends across a base of the at least one absorption layer and a base of the at least one signal receiving arrangement, and along sides of the at least one absorption layer and sides of the at least one signal receiving arrangement.

According to another preferred and non-limiting embodiment or aspect, a method of determining an inventory of an item storage and tracking unit holding a plurality of discrete items may include providing the item storage and tracking unit including a housing including a plurality of receptacles positioned therein and defining a plurality of associated inner areas, at least one signal emitting device associated with at least one item of the plurality of discrete items and configured to emit a signal, wherein the at least one item is accessible by accessing at least one receptacle of the plurality of receptacles, at least one movement sensor associated with each receptacle of the plurality of receptacles and configured to detect access to the associated receptacle, and at least one signal receiving arrangement associated with each receptacle of the plurality of receptacles. The at least one signal receiving arrangement may scan at least a portion of the inner area of the associated receptacle for the signal emitted from the at least one signal emitting device associated with the at least one item of the plurality of discrete items, wherein the scan is initiated at least partly in response to the at least one movement sensor associated with the associated receptacle detecting access to or interaction with the associated receptacle.

According to still another preferred and non-limiting embodiment or aspect, an item storage and tracking unit for holding a plurality of discrete items may include a housing including a plurality of receptacles positioned therein and defining a plurality of associated inner areas. At least one signal emitting device is associated with at least one item of the plurality of discrete items and configured to emit a signal. The at least one item is accessible by accessing at least one receptacle of the plurality of receptacles. At least one weight sensor is associated with each receptacle of the plurality of receptacles and is configured to measure a weight before an access to or interaction with the item storage and tracking unit is performed by a user and a weight after an access to or interaction with the item storage and tracking unit is performed by the user. At least one signal receiving arrangement is associated with each receptacle of the plurality of receptacles and is configured to scan at least a portion of the inner area of the associated receptacle for the signal emitted from the at least one signal emitting device associated with the at least one item of the plurality of discrete items. The scan is initiated at least partly in response to a comparison of the weight before the user access to the weight after the user access.

The signal may include a characteristic unique to the at least one item and/or a category or type of item. At least one of the plurality of items may be positionable within at least one of the inner areas in any position and/or orientation. The at least one signal emitting device may include at least one radio frequency transponder, and the at least one signal receiving arrangement comprises at least one antenna. The at least one signal receiving arrangement may be configured to not initiate a scan of the inner area of the associated receptacle for the signal emitted from the at least one signal emitting device if the at least one weight sensor associated with the associated receptacle does not sense a weight change in or associated with the associated receptacle.

The item storage and tracking unit may further include at least one movement sensor associated with each receptacle of the plurality of receptacles and configured to detect access to at least one receptacle of the plurality of receptacles. The at least one signal receiving arrangement may be configured to scan the inner area of the associated receptacle if the weight before the detected access or interaction is different from the weight after the detected access or interaction. The at least one signal receiving arrangement may be configured to not initiate a scan of the inner area of the associated receptacle if the at least one movement sensor does not detect access or interaction. The measured weight may include the weight of at least one of the following: a portion of the structure defining the inner area, a portion of the receptacle, a surface of the receptacle, at least one item of the plurality of items, or any combination thereof.

The item storage and tracking unit may further include at least one controller (or control device and/or computer) configured to directly or indirectly communicate with and/or control at least one of the following: the at least one signal emitting device, the at least one signal receiving arrangement, at least one movement sensor, the at least one weight sensor, at least one lock mechanism, at least one computer associated with the unit, at least one display associated with the unit, at least one interface associated with the unit, at least one input device associated with the unit, at least one component of the unit, or any combination thereof.

At least one surface or area of the unit may include at least one shielding element configured to minimize, redirect, and/or prevent the signal emitted from the at least one signal emitting device from passing therethrough. At least one surface defining the inner area of the associated receptacle may include at least one shielding element. The item storage and tracking unit may further include at least one absorption layer between the at least one signal receiving arrangement and the at least one shielding element. The at least one shielding element may include at least one substantially U-shaped shielding element. The item storage and tracking unit may further include at least one absorption layer between the at least one signal receiving arrangement and the at least one U-shaped shielding element. A substantially U-shaped field may extend across a base of the at least one absorption layer and a base of the at least one signal receiving arrangement, and along sides of the at least one absorption layer and sides of the at least one signal receiving arrangement. The access or interaction may be detected by the sensing of the opening a door of the unit and/or the opening a drawer of the unit.

According to another preferred and non-limiting embodiment or aspect, a method of determining an inventory of an item storage and tracking unit holding a plurality of discrete items may include providing the item storage and tracking unit including a housing including a plurality of receptacles positioned therein and defining a plurality of associated inner areas, at least one signal emitting device associated with at least one item of the plurality of discrete items and configured to emit a signal, wherein the at least one item is accessible by accessing at least one receptacle of the plurality of receptacles, at least one weight sensor associated with each receptacle of the plurality of receptacles and configured to detect weight change in or associated with the associated receptacle, and at least one signal receiving arrangement associated with each receptacle of the plurality of receptacles. The at least one signal receiving arrangement scans at least a portion of the inner area of the associated receptacle for the signal emitted from the at least one signal emitting device associated with the at least one item of the plurality of discrete items. The scan is initiated at least partly in response to a comparison of the weight before the user access to the weight after the user access.

According to still another preferred and non-limiting embodiment or aspect, an item storage and tracking unit for holding a plurality of discrete items may include a housing, at least one signal emitting device, and at least one signal receiving arrangement. The housing may include a plurality of receptacles positioned therein and defining a plurality of associated inner areas. The at least one signal emitting device may be associated with at least one item of the plurality of discrete items and configured to emit a signal, and the at least one item is accessible by accessing at least one receptacle of the plurality of receptacles. The at least one signal receiving arrangement may be associated with each receptacle of the plurality of receptacles and configured to scan at least a portion of the inner area of the associated receptacle for the signal emitted from the at least one signal emitting device associated with the at least one item of the plurality of discrete items. The scan is initiated at least partly in response to at least one user signal emitting device associated with at least one user being detected by the at least one signal receiving arrangement of the associated receptacle.

According to a preferred and non-limiting embodiment or aspect, a method of determining an inventory of an item storage and tracking unit holding a plurality of discrete items may include providing the item storage and tracking unit including a housing, at least one signal emitting device, and at least one signal receiving device. The housing may include a plurality of receptacles positioned therein and defining a plurality of associated inner areas. The at least one signal emitting device may be associated with at least one item of the plurality of discrete items and configured to emit a signal, and the at least one item is accessible by accessing at least one receptacle of the plurality of receptacles. The at least one signal receiving arrangement may be associated with each receptacle of the plurality of receptacles. The method may further include scanning, by the at least one signal receiving arrangement, at least a portion of the inner area of the associated receptacle for the signal emitted from the at least one signal emitting device associated with the at least one item of the plurality of discrete items. The scan may be initiated at least partly in response to at least one user signal emitting device associated with at least one user being detected by the at least one signal receiving arrangement of the associated receptacle.

Aspects of the present invention will now be described in the following numbered clauses:

Clause 1: An item storage and tracking unit for holding a plurality of discrete items, comprising: a housing including a plurality of receptacles positioned therein and defining a plurality of associated inner areas; at least one signal emitting device associated with at least one item of the plurality of discrete items and configured to emit a signal, wherein the at least one item is accessible by accessing at least one receptacle of the plurality of receptacles; at least one movement sensor associated with each receptacle of the plurality of receptacles and configured to detect access to the at least one receptacle; and at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to the at least one movement sensor associated with the associated receptacle detecting access to the associated receptacle.

Clause 2: The item storage and tracking unit according to clause 1, wherein the signal comprises a characteristic unique to the at least one item and/or a type of item.

Clause 3: The item storage and tracking unit according to clause 1 or clause 2, wherein at least one of the plurality of items is positionable within at least one of the inner areas in any position and/or orientation.

Clause 4: The item storage and tracking unit according to any of clauses 1-3, wherein the at least one signal emitting device comprises at least one radio frequency transponder, and the at least one signal receiving arrangement comprises at least one antenna.

Clause 5: The item storage and tracking unit according to any of clauses 1-4, wherein the at least one signal receiving arrangement is configured to not initiate a scan of the inner area of the associated receptacle for the signal emitted from the at least one signal emitting device if the at least one movement sensor associated with the associated receptacle does not detect access to the associated receptacle.

Clause 6: The item storage and tracking unit according to any of clauses 1-5, further comprising at least one weight sensor associated with each receptacle of the plurality of receptacles and configured to measure, a weight before the at least one movement sensor associated with the associated receptacle detects an access to the associated receptacle, and a weight after the at least one movement sensor associated with the associated receptacle detects an access to the associated receptacle.

Clause 7: The item storage and tracking unit according to clause 6, wherein the at least one signal receiving arrangement is configured to scan the inner area of the associated receptacle if the weight before the detected access is different from the weight after the detected access.

Clause 8: The item storage and tracking unit according to clause 6 or clause 7, wherein the at least one signal receiving arrangement is configured to not initiate a scan of the inner area of the associated receptacle if the weight before the detected access is substantially equal to the weight after the detected access.

Clause 9: The item storage and tracking unit according to any of clauses 1-8, wherein at least one surface or area of the unit comprises at least one shielding element configured to at least one of minimize, redirect, and prevent the signal emitted from the at least one signal emitting device from passing therethrough.

Clause 10: The item storage and tracking unit according to clause 9, further comprising at least one absorption layer between the at least one signal receiving arrangement and the at least one shielding element.

Clause 11: A method of determining an inventory of an item storage and tracking unit holding a plurality of discrete items, comprising: (a) providing the item storage and tracking unit, comprising: a housing including a plurality of receptacles positioned therein and defining a plurality of associated inner areas, at least one signal emitting device associated with at least one item of the plurality of discrete items and configured to emit a signal, wherein the at least one item is accessible by accessing at least one receptacle of the plurality of receptacles, at least one movement sensor associated with each receptacle of the plurality of receptacles and configured to detect access to the associated receptacle, and at least one signal receiving arrangement associated with each receptacle of the plurality of receptacles; and (b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to the at least one movement sensor associated with the associated receptacle detecting access to the associated receptacle.

Clause 12: An item storage and tracking unit for holding a plurality of discrete items, comprising: a housing including a plurality of receptacles positioned therein and defining a plurality of associated inner areas; at least one signal emitting device associated with at least one item of the plurality of discrete items and configured to emit a signal, wherein the at least one item is accessible by accessing at least one receptacle of the plurality of receptacles; at least one weight sensor associated with each receptacle of the plurality of receptacles and configured to measure a weight before an access to the item storage and tracking unit is performed by a user and a weight after an access to the item storage and tracking unit is performed by the user; and at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to a comparison of the weight before the user access to the weight after the user access.

Clause 13: The item storage and tracking unit according to clause 12, wherein at least one of the plurality of items is positionable within at least one of the inner areas in any position and/or orientation.

Clause 14: The item storage and tracking unit according to clause 12 or clause 13, further comprising at least one movement sensor associated with each receptacle of the plurality of receptacles and configured to detect access to at least one receptacle of the plurality of receptacles.

Clause 15: The item storage and tracking unit according to clause 14, wherein the at least one signal receiving arrangement is configured to not initiate a scan of the inner area of the associated receptacle if the at least one movement sensor does not detect access.

Clause 16: The item storage and tracking unit according to any of clauses 12-15, wherein the access is detected by the sensing of at least one of the opening a door of the unit and the opening a drawer of the unit.

Clause 17: A method of determining an inventory of an item storage and tracking unit holding a plurality of discrete items, comprising: (a) providing the item storage and tracking unit comprising: a housing including a plurality of receptacles positioned therein and defining a plurality of associated inner areas, at least one signal emitting device associated with at least one item of the plurality of discrete items and configured to emit a signal, wherein the at least one item is accessible by accessing at least one receptacle of the plurality of receptacles, at least one weight sensor associated with each receptacle of the plurality of receptacles and configured to detect weight change in or associated with the associated receptacle, and at least one signal receiving arrangement associated with each receptacle of the plurality of receptacles; and (b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to a comparison of the weight before the user access to the weight after the user access.

Clause 18: An item storage and tracking unit for holding a plurality of discrete items, comprising: a housing including a plurality of receptacles positioned therein and defining a plurality of associated inner areas; at least one signal emitting device associated with at least one item of the plurality of discrete items and configured to emit a signal, wherein the at least one item is accessible by accessing at least one receptacle of the plurality of receptacles; and at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to at least one user signal emitting device associated with at least one user being detected by the at least one signal receiving arrangement of the associated receptacle.

Clause 19: A method of determining an inventory of an item storage and tracking unit holding a plurality of discrete items, comprising: (a) providing the item storage and tracking unit comprising: a housing including a plurality of receptacles positioned therein and defining a plurality of associated inner areas, at least one signal emitting device associated with at least one item of the plurality of discrete items and configured to emit a signal, wherein the at least one item is accessible by accessing at least one receptacle of the plurality of receptacles, at least one signal receiving arrangement associated with each receptacle of the plurality of receptacles; and (b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to at least one user signal emitting device associated with at least one user being detected by the at least one signal receiving arrangement of the associated receptacle.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Further features and other objects and advantages will become apparent from the following detailed description made with reference to the drawings in which:

FIG. 3A is a schematic view of a portion of a shelving system of an item storage and tracking cabinet according to principles of the present invention;

FIG. 3B is a schematic view of a portion of a shelving system of an item storage and tracking cabinet according to principles of the present invention;

DETAILED DESCRIPTION OF THE PREFERRED EMBODIMENT OR ASPECTS

Figure 1:
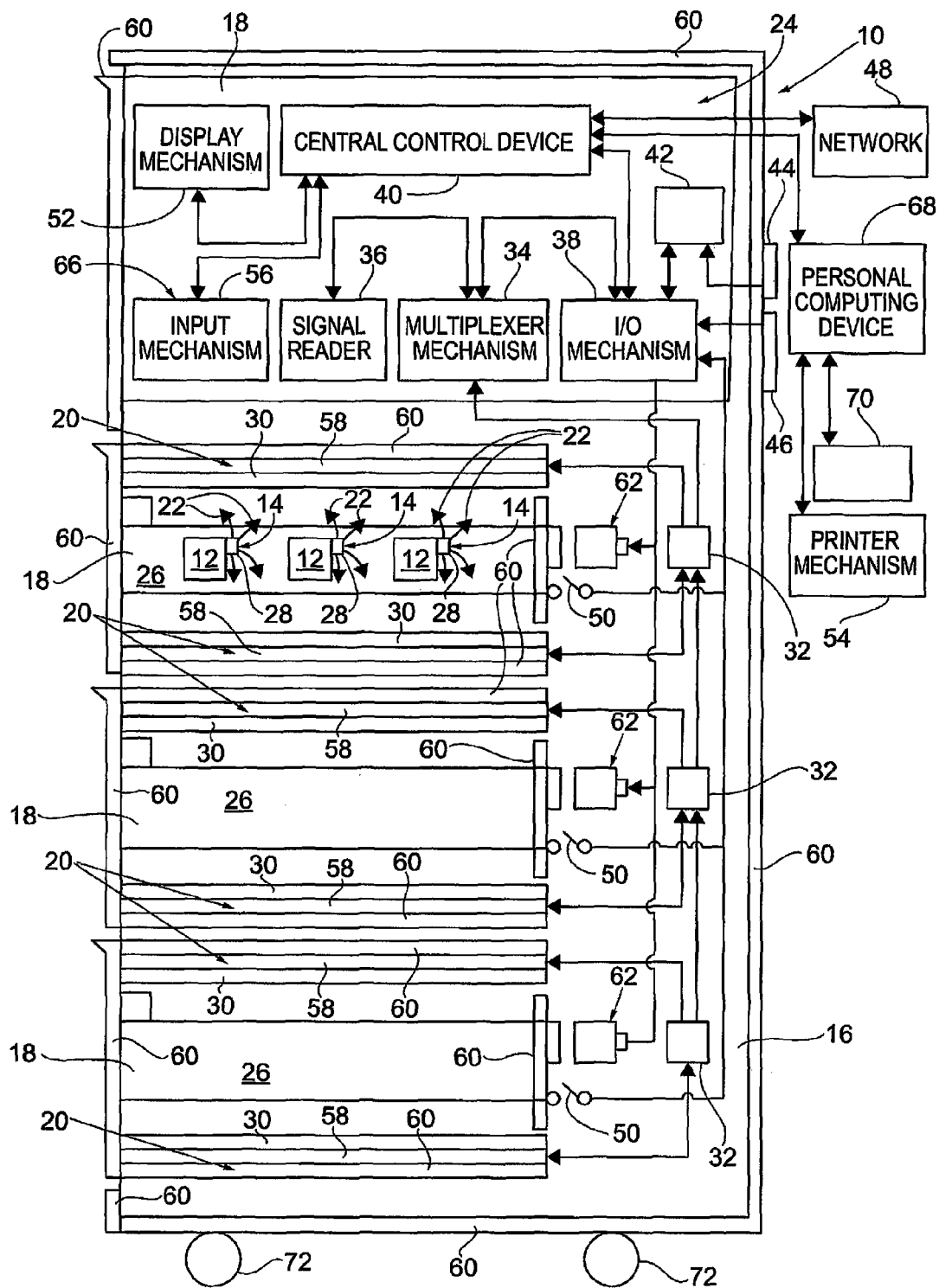
FIG. 1 is a schematic view of a preferred embodiment or aspect of an item storage and tracking cabinet according to principles of the present invention.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiment or aspects of the invention. Hence, specific dimensions and other physical characteristics related to the embodiment or aspects disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

U.S. patent application Ser. Nos. 10/209,348; 12/240,022; 13/158,827 (issued as U.S. Pat. No. 8,547,203); and Ser. No. 14/013,625 are all directed to a "Dynamic Control Containment Unit," and are incorporated by reference herein in their entirety. U.S. patent application Ser. No. 12/607,732 (issued as U.S. Pat. No. 8,414,471); and Ser. No. 13/793,201 are both directed to an "Endoscope Storage Cabinet, Tracking System, and Signal Emitting Member," and are incorporated by reference herein in their entirety.

In one preferred and non-limiting embodiment or aspect, provided is an item storage and tracking unit 10 for holding multiple, discrete items 12, as illustrated in FIGS. 1 and 2. Each of the items 12 has a signal emitting device 14 associated therewith. The item storage and tracking unit 10 includes a housing 16 having multiple receptacles 18, which are accessible to a user. The items 12 and their associated signal emitting devices 14 are at least partially contained or supported within the receptacles 18. The item storage and tracking unit 10 may be dynamic, in that the items 12 can be placed in any position and/or orientation in any receptacle 18. Therefore, the items 12 do not have to be placed in predetermined locations or receptacles 18, such as assigned bins, slots, and/or the like.

A signal receiving mechanism 20 is in communication with the receptacles 18 and receives signals 22 emanating from the signal emitting devices 14. A controller 24 (or central control device 40) is in communication with the signal receiving mechanism 20 and is able to initiate or implement various actions based upon the content of the signals 22 received by the signal receiving mechanism 20. The receptacle 18 may be a drawer, a shelf 26, a box, a container, and/or the like. Further, the items 12 may be objects, supplies, assets, instruments, medical equipment, medical supplies, medical assets, medical instruments, and/or the like. Further, the controller 24 may be in the form of or include a central control device 40, which may be in the form of a computer or computing device, which includes at least one processor and program instructions stored on at least one non-transitory storage medium, such that, when the program instructions are executed by the at least one processor, the at least one processor implements or executes the various actions and steps discussed herein. Further, the controller 24 (or central control device 40) may include the necessary hardware, firmware, and/or software, to implement or execute the various actions and steps discussed herein, such that the controller 24 (or central control device 40) represents a specially-programmed computing device.

Figure 2A:
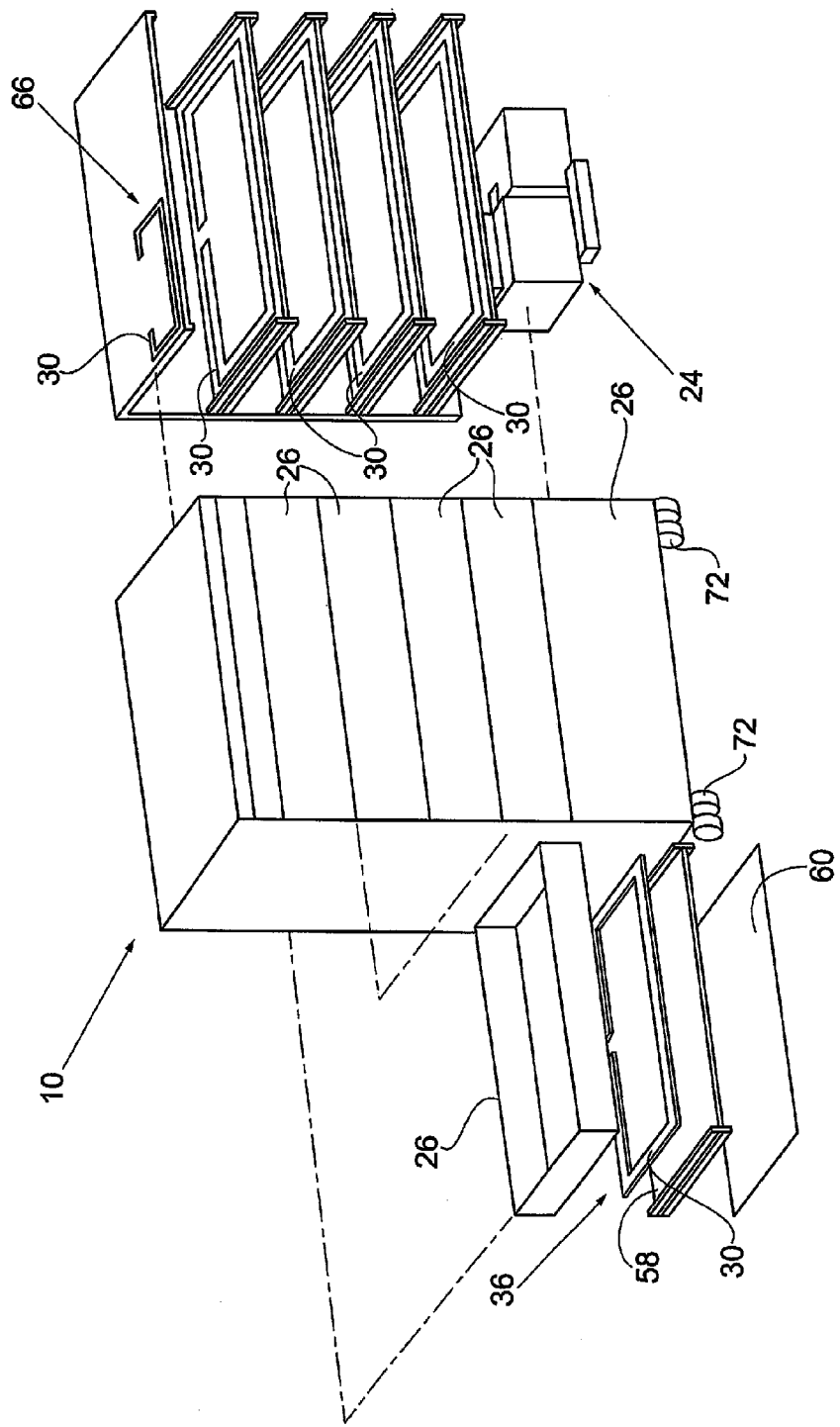
FIG. 2A is an exploded, perspective view of another embodiment or aspect of an item storage and tracking cabinet according to principles of the present invention.
Figure 2B:
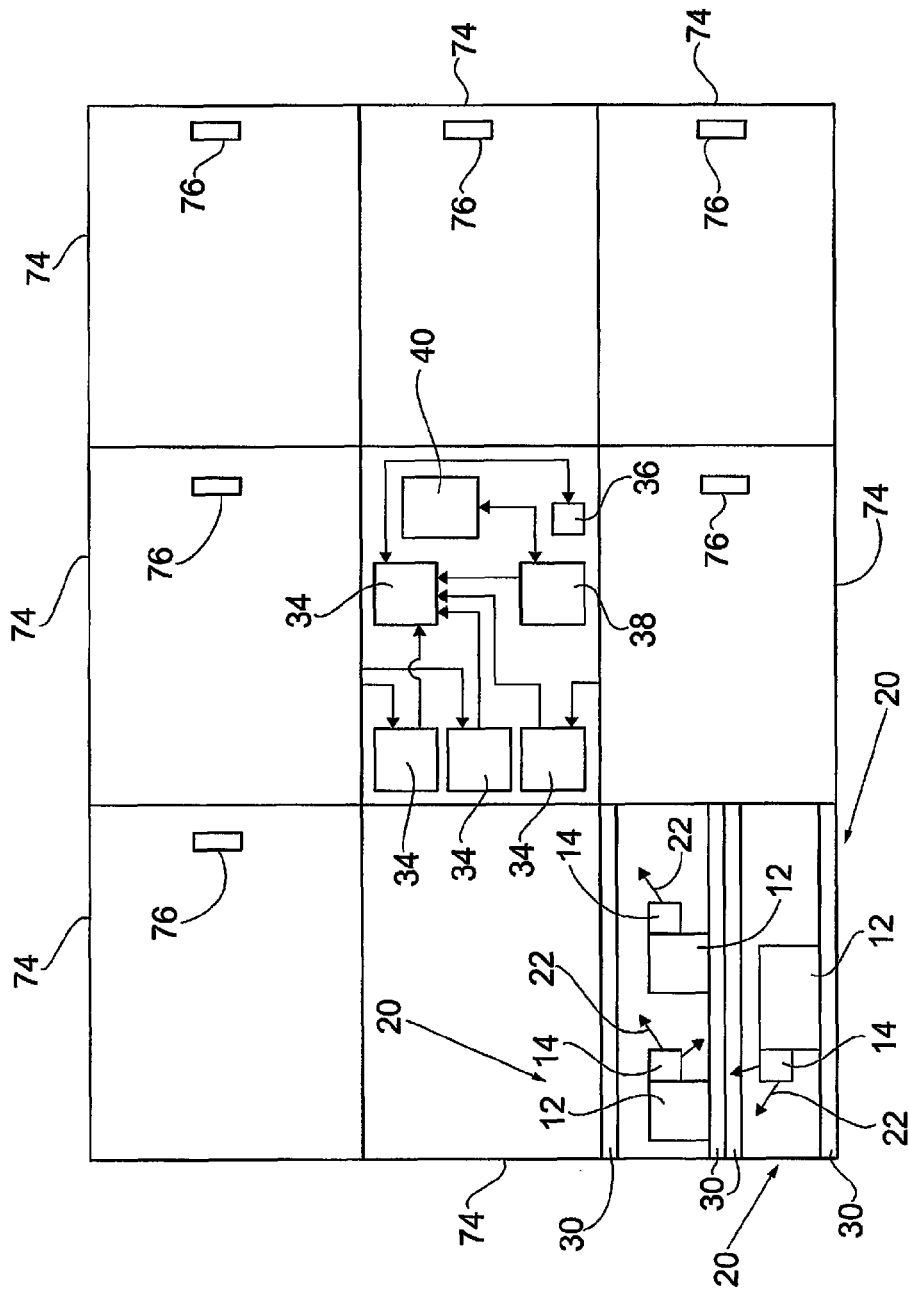
FIG. 2B is a schematic view of still another preferred embodiment or aspect of an item storage and tracking cabinet according to principles of the present invention.
Figure 4:
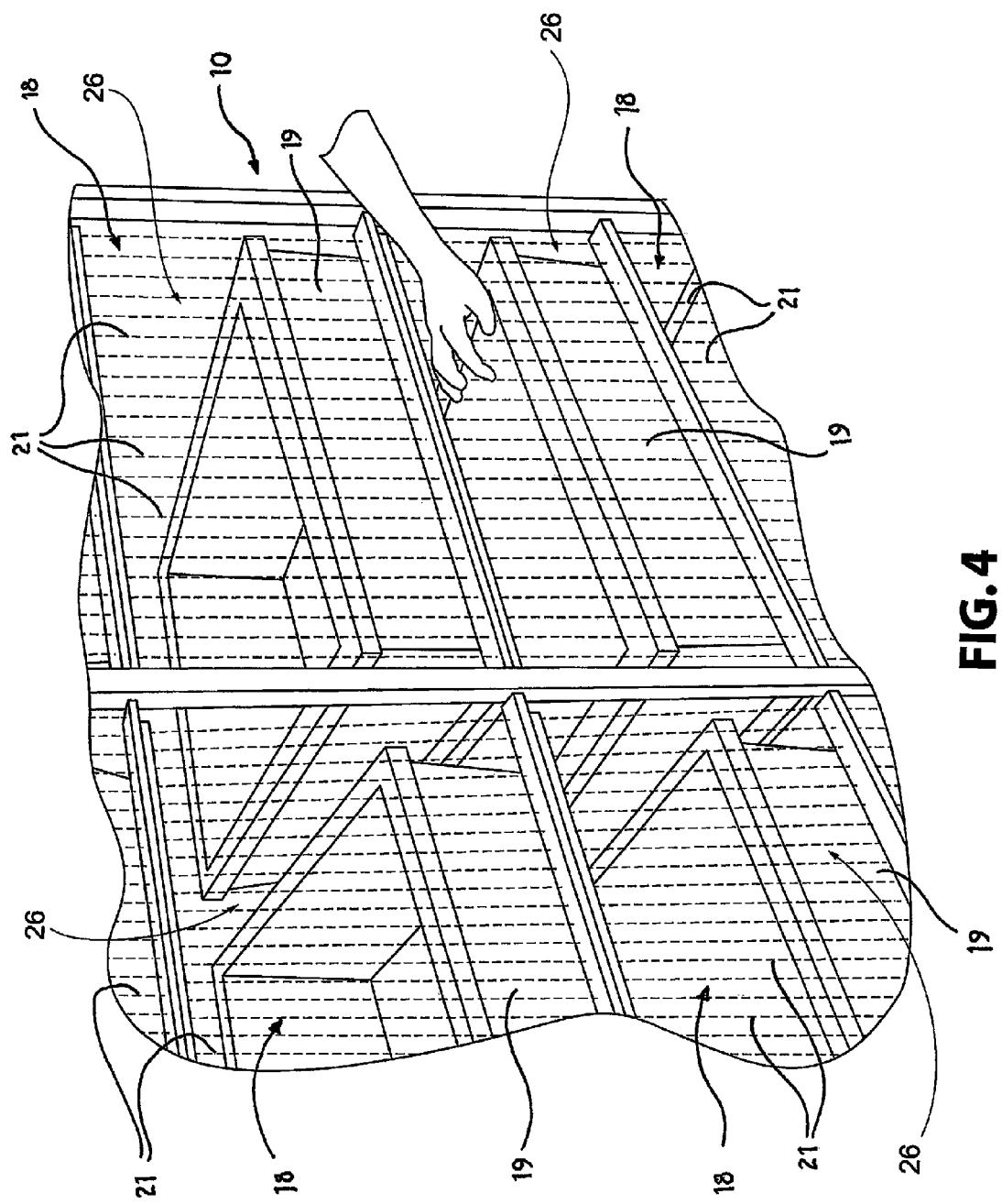
FIG. 4 is a perspective view of a portion of a shelving system of an item storage and tracking cabinet according to principles of the present invention.

In one preferred and non-limiting embodiment or aspect, the receptacle 18 is in the form of or includes a shelf 26. The shelf 26 may be slidable with respect to the housing 16, such that the shelf 26 may be slid open to extend at least partially outside the housing 16 to provide easier access to the items 12 contained therein. Alternatively, the shelf 26 may be fixed in the housing 16, such that a user must reach at least partially into the housing 16 to add, remove, or otherwise interact with the items 12 contained on or in the shelf 26. In a preferred and non-limiting embodiment or aspect, the signal emitting devices 14 are radio frequency identification (RF/ID) transponders 28. Each of the RF/ID transponders 28 is attached to or associated with an individual item 12 or, optionally, a category or type of item 12. Further, each of the RF/ID transponders 28 emit a signal 22 that is unique to the item 12 (and/or category or type of item 12) to which the RF/ID transponder 28 is attached or associated. After the RF/ID transponder 28 has been attached or associated with the item 12, it is placed in a receptacle 18 or on a shelf 26. Although FIG. 1 illustrates three item-containing shelves 26, any number of shelves 26 may be utilized, and the number of shelves 26 does not affect the functionality of the item storage and tracking unit 10. In particular, any number of rows of shelves 26 and any number of columns of shelves 26 may be utilized. For example, although a single column of shelves 26 with multiple rows is shown in FIGS. 1 and 2, multiple columns and multiple rows may be utilized as shown in FIGS. 2B and 4. Further, and as illustrated in FIG. 4, the items 12 may be placed in a bin 19 or container, which is positioned on or within one or more receptacles 18 or shelves 26.

In still another preferred and non-limiting embodiment or aspect, and as illustrated in FIG. 2B, the control containment unit 10 and, in particular, the housing 16, may take the form of a cabinet with multiple access points. In one exemplary embodiment or aspect, the receptacle 18 is a shelf 26 (or, as shown in FIG. 4, a bin 19 or container positioned on or within each receptacle 18 or shelf 26) and each shelf 26 may have one or more antennae 30, as described in further detail below, for receiving signals 22 from the signal emitting devices 14 attached to the items 12. A door 74 or other cover may optionally be used to prevent and/or control access to the receptacles 18. The door 74 may have a handle 76 to allow a user to open the door 74. Alternatively, the doors 74 may be omitted and the receptacles 18 or shelves 26 may be directly accessible to a user, as shown in FIG. 4; and, as discussed, a bin or other container may be placed on or within the receptacle 18 or shelf 26. Also, and as discussed, the shelves 26 may be slidable with respect to the housing 16.

In a preferred and non-limiting embodiment or aspect, and as illustrated in FIG. 1, the signal receiving mechanism 20 comprises at least one antenna 30 configured to receive the radio frequency signals 22 emanating from the RF/ID transponders 28. Although a single antenna 30 may be placed underneath each receptacle 18 or shelf 26, such that the antenna 30 is dedicated to receiving signals 22 emanating from an assigned receptacle 18 or shelf 26, as illustrated in FIGS. 2A and 3A, in a preferred and non-limiting embodiment or aspect, two antennae 30 can be used for each receptacle 18 or shelf 26—one antenna 30 immediately above the receptacle 18 or shelf 26, and one antenna 30 immediately below the receptacle 18 or shelf 26, as shown in FIGS. 1 and 3B, such that each pair of antennas is dedicated to receiving signals 22 emanating from an assigned receptacle 18 or shelf 26. This multiple-antenna arrangement for each receptacle 18 or shelf 26 enables the signal receiving mechanism 20 to passively receive the signals 22, as opposed to relying upon the specific movement of an item 12 across a stationary reading device, and provides greater accuracy in receiving the signals 22 from the signal emitting devices 14 or RF/ID transponders 28. When the items 12 are in a receptacle 18 or shelf 26 and within the housing 16, the items 12 (and subsequently the RF/ID transponders 28) are positioned in the item storage and tracking unit 10, such that they are located in the antenna 30 field assigned to the receptacle 18 or shelf 26. Alternatively, or additionally, an antenna pair may be placed at a front of each receptacle 18 or shelf 26, e.g., on door 74, as shown in FIG. 2B, and at a back of each receptacle 18 or shelf 26 opposite the door 74. The RF/ID transponders 28 are energized by the antenna 30 field and emit a radio frequency signal 22 corresponding to the unique identification of the transponders 28, typically an identification number or other specified data. The signals 22 are picked up by the antennae 30 assigned to the receptacle 18 or shelf 26 and communicated to the controller 24 (or central control device 40).

Although the signals 22 emanating from the signal emitting devices 14 typically have a characteristic unique to a specific item 12, it is also envisioned that the signal emitting devices 14 may emit signals 22 unique to a category, type, group, set, or other association of multiple items 12.

In one preferred and non-limiting embodiment or aspect, the controller 24 (or central control device 40) is in communication with a tuning mechanism 32. The tuning mechanism 32 is used to set a frequency parameter of the signal receiving mechanism 20 or antenna 30. The receptacles 18 or shelves 26 may also have an associated indicator light (not shown), possibly on outside surfaces thereof, to indicate which receptacle(s) 18 a user has permission to access. Further, the unit 10 and/or one or more of the receptacles 18 or shelves 26, may include a user interface or display screen in communication with the controller 24 (or central control device 40) to provide information about the contents of the specific receptacle 18 or shelf 26, for example, a number of items in the receptacle 18 or shelf 26, a type of each item in the receptacle 18 or shelf 26, a user that is requesting permission to access the receptacle 18 or shelf 26, and/or a user who last accessed the receptacle 18 or shelf 26; and/or to enable the user to enter notes about the items 12 on the receptacle 18 or shelf 26. Accordingly, a user may avoid unnecessary searching of a receptacle 18 or shelf 26 for an item 12 that is not contained therein and, thus, unnecessary scanning may be avoided to update the number of items in the shelf 26.

In a preferred and non-limiting embodiment or aspect the controller 24 (or central control device 40) includes a multiplexor mechanism 34 that is in communication with the signal receiving mechanism 20 or antennae 30 assigned to each receptacle 18 or shelf 26, and provides an output signal corresponding to the signal 22 received by the signal receiving mechanism 20. The multiplexor mechanism 34 is also in communication with a signal reader mechanism 36. The signal reader mechanism provides an output signal corresponding to the signal received by the multiplexor mechanism 34. An input/output mechanism 38 is in communication with the multiplexor mechanism 34 and/or the signal reader mechanism 36 and translates output signals into digital output signals. The central control device 40 is in communication with the input/output mechanism 38 and receives, processes, and transmits signals, as well as initiates or implements actions, based upon the digital output signals received from the input/output mechanism 38.

In one preferred and non-limiting embodiment or aspect, the signals 22 received by the antennae 30 are sent through the multiplexor mechanism 34 to the signal reader mechanism 36, which is an internally-located RF/ID reader. The multiplexor mechanism 34 collects signals from more than one antenna 30 and communicates with a single signal reader mechanism 36. In addition, the multiplexor mechanism 34 allows each antenna 30 to be uniquely addressable and subsequently individually controlled by the controller 24 (or central control device 40), such that individual shelves 26 may be separately scanned one at a time and the contents of each shelf 26 separately inventoried or categorized by the controller 24 (or central control device 40). The signal reader mechanism 36 decodes the signal, and communicates this decoded signal to the central control device 40 via the input/output mechanism 38. The central control device 40 identifies the signals 22, associates the signals 22 with the correct items 12 and/or shelves 26, and logs the identification of the items 12 into an inventory database, maintained on the central control device 40.

The controller 24 (or central control device 40) may include a power control module 42, which is in communication with the input/output mechanism 38. The power control module 42 provides specified power outputs at specified power levels to the various components of the controller 24 (or central control device 40). Further, the power control module 42 may be operated or activated by a single power switch 44. Therefore, a user need only operate a single power switch 44 to power all the various components of the controller 24 (or central control device 40) and the item storage and tracking unit 10. The item storage and tracking unit 10 may also include a backup power module 46 in communication with the input/output mechanism 38 in order to supply power in the event of an electronic power failure.

The central control device 40 may be a computer, a computing device, a programmable microchip, a microcontroller, a personal computer, a hand-held computer, a terminal, a network computing device, and/or the like. Further, and as discussed above, the central control device 40 (or controller 24) may be in the form of a computer or computing device, which includes at least one processor and program instructions stored on at least one non-transitory storage medium, such that, when the program instructions are executed by the at least one processor, the at least one processor implements or executes the various actions and steps discussed herein. Further, the central control device 40 (or controller 24) may include the necessary hardware, firmware, and/or software, to implement or execute the various actions and steps discussed herein, such that the central control device 40 (or controller 24) represents a specially-programmed computing device. When used in a network relationship, the central control device 40 communicates with a network 48, which enables a user or system administrator to administrate, control, and/or manage multiple item storage and tracking units 10 throughout a building.

The item storage and tracking unit 10 may include a switch mechanism 50 that is in operable communication with each of the receptacles 18 or shelves 26. As a user is accessing a particular receptacle 18 or shelf 26, the switch mechanism 50 for that receptacle 18 or shelf 26 moves to an open position, for example in response to a sensor array (shown in FIGS. 3-6) being triggered, and indicates to the central control device 40 via the input/output mechanism 38, that the particular receptacle 18 or shelf 26 has been accessed. As disclosed in more detail below, the switch mechanism 50 may be operated in response to a movement sensor 102 and/or a weight sensor 104 or the shelf (or bin) itself. Alternatively, the item storage and tracking unit 10 may not include the switch mechanism 50, and the sensor array, e.g., movement sensor 102 and/or the weight sensor 104 described in more detail below, may communicate directly with the input/output mechanism 38 or the central control device 40 (such as through movement of the user's hand into or out of the receptacle 18 or shelf 26, movement of a portion of the receptacle 18 or shelf 26 with respect to the sensor, and/or some other interaction with the receptacle 18 or shelf 26). The central control device 40, or program instructions contained thereon, sends signals to the multiplexor mechanism 34, commanding it to begin reading input from the antennae 30 associated with the particular shelf 26 that has been accessed and/or opened. By comparing the inventory of the shelf 26 before and after it is accessed, the central control device 40 may identify items 12 removed from or added to the receptacle 18 or shelf 26.

In one preferred and non-limiting embodiment or aspect, the item storage and tracking unit 10 includes a display mechanism 52 in communication with the central control device 40 for providing a visual display to a user. Data and information may be displayed to the user, whether in graphical or textual format, on the display mechanism 52. For example, the display mechanism 52 may display an action initiated by the central control device 40, a use history, an item 12 history, a user history, user data, item 12 data, inventory data, receptacle 18 or shelf 26 data, item storage and tracking unit 10 data, a receptacle 18 or shelf 26 inventory, an item storage and tracking unit 10 inventory, and/or the like. In a preferred and non-limiting embodiment or aspect, the display mechanism 52 is located on the housing 16 at an area easily viewable by a user. However, the display mechanism 52 may be a monitor positioned on or adjacent to the item storage and tracking unit 10. In a preferred and non-limiting embodiment or aspect, the display mechanism 52 may automatically display a location of an item 12, e.g., a particular receptacle 18 or shelf 26, that is associated with a particular user, in response to that user accessing the unit 10 with his or her RF/ID badge or some user-specific access code to allow the user to more quickly locate often-accessed items 12.

The item storage and tracking unit 10 also may include a printer mechanism 54, which is in communication with the central control device 40, for providing visual printouts corresponding to the information processed by the central control device 40. For example, any of the information discussed above in connection with the display mechanism 52 may also be printed out in a physical format by the printer mechanism 54.

In another preferred and non-limiting embodiment or aspect, the item storage and tracking unit 10 includes an input mechanism 56 in communication with the central control device 40, which is capable of receiving user input and transmitting user input signals to the central control device 40. The input mechanism 56 may be a keypad, a touch display, a personal computing device, a hand-held computing device, a magnetic reading device, a radio frequency identification reading device, a bar code reading device, a light pen, a keyboard, a mouse, a terminal, voice activation/verification, biometric readers, etc. In a preferred and non-limiting embodiment or aspect, the input mechanism 56 is positioned adjacent or near the display mechanism 52, thereby allowing a user to visually see his or her input as the input mechanism 56 receives the data. As with the display mechanism 52, the input mechanism 56 is positioned at a convenient area, easily accessible by many users. The input mechanism 56 may also be in communication with an antenna 30, which enables a user to provide initial radio frequency identification signals for each item 12 to the central control device 40.

In a preferred and non-limiting embodiment or aspect, each antenna 30, which receives the radio frequency signals 22 emanating from the signal emitting devices 14 or the RF/ID transponders 28, is positioned substantially adjacent its assigned receptacle 18 or shelf 26 by an absorber material 58. As seen in FIGS. 2A and 3, an antenna 30 is rested upon or attached to the absorber material 58 when used in connection with the bottom antenna 30 of the assigned receptacle 18 or shelf 26, and is attached to the absorber material 58 when used in connection with the top antenna 30 of the assigned receptacle 18 or shelf 26. Of course, this absorber material 58 may be used in connection with an antenna 30 positioned anywhere on or in connection with the receptacle 18 or shelf 26, such as on any of the front, back, or sides of the receptacle or shelf 26.

Still referring to FIGS. 1, 2A and 3, and in another preferred and non-limiting embodiment or aspect, on at least one side of the absorbing material 58 opposite the antenna 30, is a shielding layer or element 60. In a preferred and non-limiting embodiment or aspect, as shown in FIGS. 3A and 3B, the shielding element 60 may be a substantially U-shaped shielding element 60 with sides extending in a vertical direction to cover lateral sides of the absorbing material 58 and the antenna 30, so as to isolate the RF field of the antenna 30 from other antennae. U-shaped shielding elements 60 may cover all four lateral sides of the absorbing material 58 and/or antenna 30, or alternatively, only specified ends of the absorbing material 58 and/or antenna 30. The shielding element 60 is configured to minimize, redirect, and/or prevent the signal emitted from the at least one signal emitting mechanism 20 from passing therethrough. In a preferred embodiment or aspect, the sides of the U-shaped shielding element extend beyond the lateral sides of the absorbing material 58 and the antenna 30 in the vertical direction, i.e., upwards from a bottom antenna and downwards from a top antenna. The "U" shape reduces leakage as compared to other shapes of shield construction. The U-shaped shielding element 60 prevents signals from the antenna 30 and/or the signal emitting devices 14 from passing therethrough. The item storage and tracking unit 10 itself may be constructed of a material that functions as a shielding layer or element 60 and be lined at portions thereof with absorber material 58. For example, the entirety of the housing 16, including any divisions forming the receptacles 18 or shelves 26, as well as any doors 74, may include shielding layers or elements 60, or a similarly functioning material. The housing 16 may be lined with the absorber material 58 at locations corresponding to the antennae 30.

A distance between the antenna 30 and the base of the shielding element 60 should be far enough for the antenna to operate properly, when the shielding layer or element 60 is a metal shielding layer or element 60. Specifically, if the antenna 30 is too close to the metal, the antenna 30 may become disabled and/or unusable. The absorber material 58 prevents this effect. The absorber material 58 reduces a space required for the shielding material of the shielding element 60, and the space required between the shielding element 60 and the antenna 30. The combination of the absorber material 58 and the shielding layer or element 60 prevents items 12 in other receptacles 18 or shelves 26 located above, below and/or to the sides of the object shelf 26 from being read during a reading process. This prevents confusion by the central control device 40 and isolation of each individual receptacle 18 or shelf 26. Not only may each receptacle 18 or shelf 26 have at least one shielding layer or element 60 associated with each antenna 30 assigned thereto, the item storage and tracking unit 10, and specifically the housing 16, may also include additional shielding layers or elements 60, which may or may not be U-shaped, to ensure that signals emanating from all of the receptacles 18 or shelves 26 do not pass through the housing 16 of the item storage and tracking unit 10 (and impact an adjacently positioned item storage and tracking unit 10).

In one preferred and non-limiting embodiment or aspect, and as illustrated in FIGS. 3A and 3B, each of the receptacles 18 or shelves 26 may be associated with a sensor array. That is, each receptacle 18 or shelf 26 may be associated with a movement sensor 102 (e.g., a movement sensor device, a movement sensor array, a signal interaction detection device, a signal interaction detection sensor array, and/or the like) that is configured to directly or indirectly communicate with and/or control the antenna 30 of that receptacle 18 or shelf 26 to scan items 12 on or in the receptacle 18 or shelf 26. Each movement sensor 102 is configured to detect movement to determine user access to a receptacle 18 or shelf 26 (e.g., a user's hand or other object has reached into the receptacle 18 or shelf 26, a portion of the receptacle 18 or shelf 26 has been moved out of or away from the item storage and tracking unit 10, and/or the like). For example, as shown in FIG. 4, and in a preferred and non-limiting embodiment or aspect, the movement sensor 102 may emit one or more laser light 21 across a plane which may be broken by a user (whether a portion of the user and/or a portion of the receptacle 18 or shelf 26) to access the item storage and tracking unit 10. If the movement sensor 102 detects movement, e.g., the movement sensor 102 detects that the laser light 21 is broken or interrupted to access the receptacle 18 or shelf 26 to add or remove an item 12 to or from the receptacle 18 or shelf 26, or the receptacle 18 or shelf 26 (or drawer) is moved with respect to the housing 16, the movement sensor 102 is triggered or activated. The movement sensor 102 may include laser light emitters 103 at one side of the receptacle 18 or shelf 26 and laser light receivers 105 at an opposite side of the receptacle 18 or shelf 26 or, alternatively, laser light emitters 103 and laser light receivers 105 at the one side of the receptacle 18 or shelf 26, and a mirror (not shown) at the opposite side of the receptacle 18 or shelf 26 configured to reflect the laser light 21. If the laser light receivers 105 do not receive one or more of the laser lights 21 emitted from the laser light emitters 103, the movement sensor 102 may determine that the plane to access the receptacle 18 or shelf 26 has been broken or interrupted. In one preferred and non-limiting embodiment or aspect, the control device 24 may control only the particular antennae 30 associated with that receptacle 18 or shelf 26 to scan the receptacle 18 or shelf 26 after access to that specific receptacle 18 or shelf 26 (or the unit 10) has ended or been sensed, and the other antennae 30 for the other receptacles 18 or shelves 26 may remain inactive. As noted above, a switch mechanism 50 may be operated in response to the movement sensor 102 to indicate to the central control device 40 that movement is detected. Alternatively, the item storage and tracking unit 10 may not include the switch mechanism 50, and the movement sensor 102 may send signals directly to the input/output mechanism 38 or the central control device 40 to indicate that movement is detected.

The movement sensor 102 may alternatively include a passive infrared sensor, an ultrasonic sensor, a microwave sensor, a tomographic motion detector, and/or any other known motion detector device. As a further alternative, the movement sensor 102 may be in the form of a physical barrier, for example, a transparent sheet or curtain, e.g., a plastic sheet, or strips, hanging in front of the receptacle 18 or shelf 26 that trigger the movement sensor 102 electrically or mechanically when moved by the user or a moveable receptacle 18 or shelf 26. In an embodiment or aspect including doors 74 and/or handles 76, opening of the door 74 and/or handle 76 may trigger the movement sensor 102, or alternatively, send a signal directly to the input/output mechanism 38 or the central control device 40 to indicate that the particular receptacle 18 or shelf 26 has been accessed.

Figure 5:
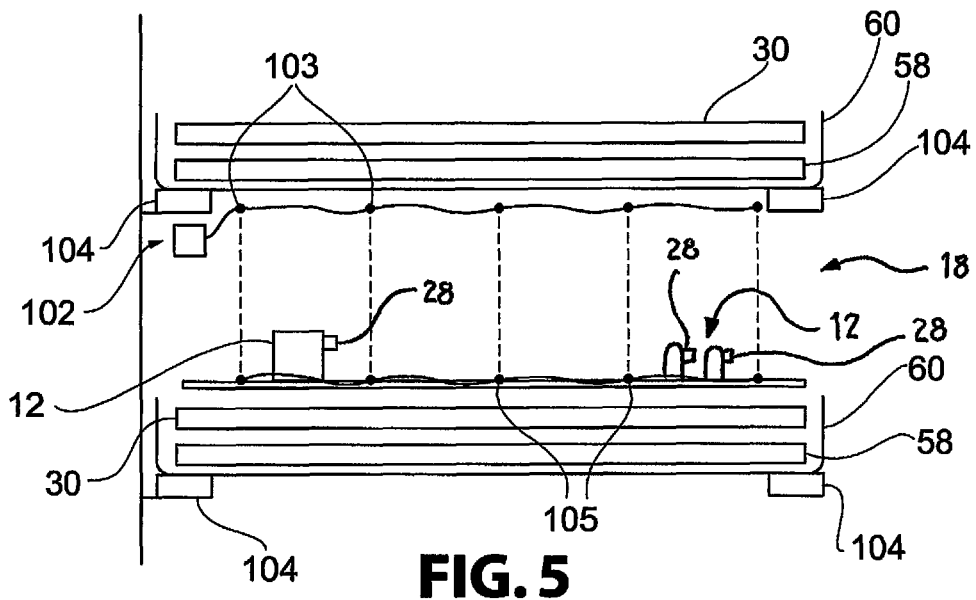
FIG. 5 is a schematic view of a portion of a shelving system of an item storage and tracking cabinet according to principles of the present invention.
Figure 6:
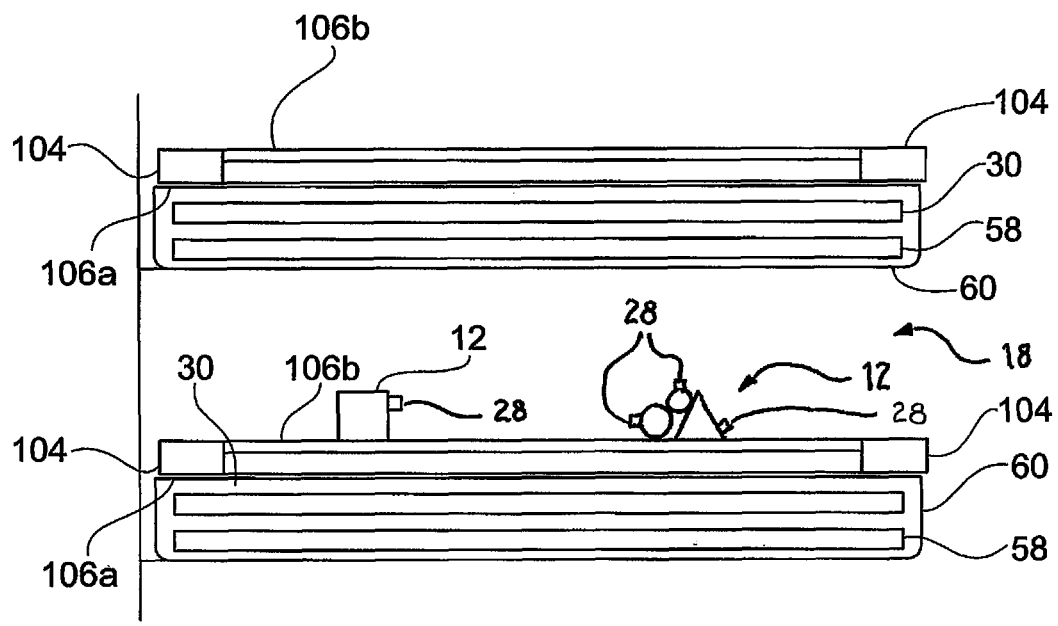
FIG. 6 is a schematic view of a portion of a shelving system of an item storage and tracking cabinet according to principles of the present invention.

As shown in FIGS. 5 and 6, each receptacle 18 or shelf 26 may (alternatively or additionally) include at least one weight sensor 104. The weight sensor 104 may be attached to a bottom side of each bottom shielding member 60 opposite the absorber material 58, as shown in FIG. 5, and may rest on the lower surface of the inner area of the receptacle 18 or shelf 26 itself. Alternatively, and as shown in FIG. 6, the weight sensor 104 may be attached to or rest on a platform 106a on a top side of the antenna 30 opposite to the absorber material 58 and covering the shielding member 60. The weight sensor 104 may include a platform 106b on which the items 12 may be positioned in the inner area of the receptacle 18 or shelf 26. Each of the platforms 106a and 106b is configured to allow the signals transmitted from the signal emitting devices 14 and the antenna 30 to pass therethrough. Certain preferred and non-limiting embodiment or aspects include attaching or associating the weight sensor 104 with at least a portion of a surface defining the inner area of the receptacle 18 or shelf 26, attaching or associating the weight sensor 104 with at least a portion of the antenna 30 associated with the receptacle or shelf 26, attaching or associating the weight sensor 104 with at least a portion of the shielding layer or element 60 associated with the receptacle or shelf 26, attaching or associating the weight sensor 104 with at least a portion of a platform 106b associated with the receptacle or shelf 26, and/or any combination thereof.

Figure 7:
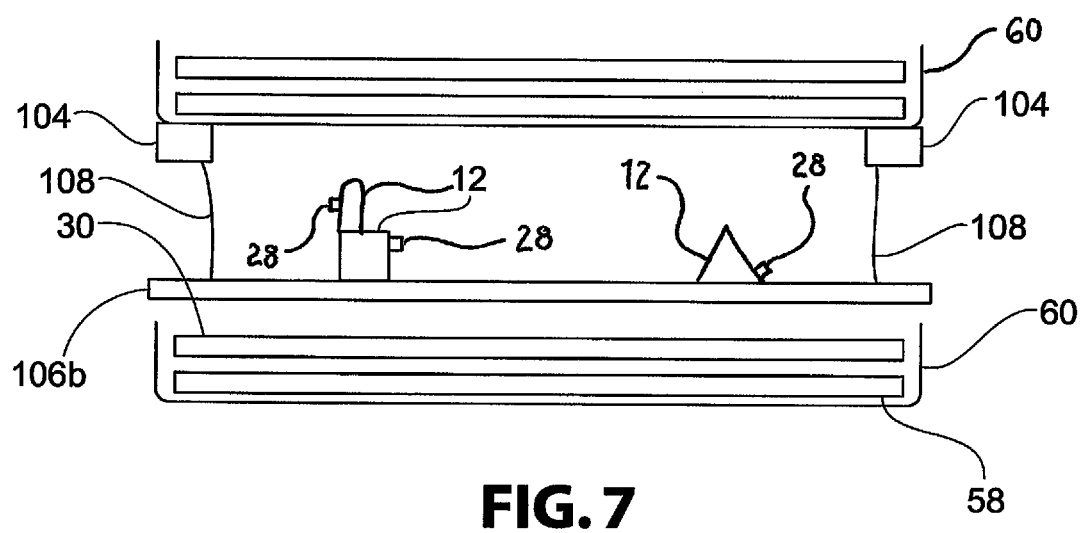
FIG. 7 is a schematic view of a portion of a shelving system of an item storage and tracking cabinet according to principles of the present invention.

In one preferred and non-limiting embodiment or aspect, at least one weight sensor 104, as shown in FIGS. 5 and 6 may be attached to a shielding layer or member 60 (see, e.g., FIG. 5) or an antenna 30 at the bottom of the receptacles 18 or shelves 26, or attached to a platform 106b positioned at the bottom of the receptacles 18 or shelves 26 (see, e.g., FIG. 6). In another preferred and non-limiting embodiment or aspect, at least one weight sensor 104, as shown, for example, in FIG. 7, may include the platform 106b connected by cables 108 to the weight sensor 104, which is attached to another portion of the receptacle 18, shelf 26, or unit 10, e.g., to the shielding layer or member 60 or an antenna 30 at the top of the receptacles 18 or shelves 26. The cables 108 may be configured such that the platform 106b may hang at any height above the bottom of receptacle 18 or shelf 26. A plurality of platforms 106b may be connected at intervals to the cables 108 to provide multiple sub-shelves in each receptacle 18 or shelf 26.

In one preferred and non-limiting embodiment or aspect, the weight sensor 104 is configured to detect or measure a weight of the items 12 in the receptacle 18 or shelf 26 before and after each trigger event, or activation of the movement sensor 102, for that receptacle 18 or shelf 26. The measured weight is the weight of at least one of the following: a portion of the structure defining the inner area, a portion of the receptacle 18 or shelf 26, a surface of the receptacle 18 or shelf 26, at least one item of the plurality of items 12, or any combination thereof. For example, the weight sensor 104 may regularly measure the weight of the items 12 in or on the receptacle 18 or the shelf 26 at periodic intervals to obtain a pre-trigger event weight, and measure the weight of the items 12 on the receptacle 18 or shelf 26 after the trigger event; for example, after access to the receptacle 18 or shelf 26 (or the unit 10) has ended, to obtain a post-trigger event weight. A post-trigger event weight for an earlier access to the receptacle 18 or shelf 26 may be used as a pre-trigger event weight for a later access to that receptacle 18 or shelf 26.

The weight sensor 104 or the central control device 40 is programmed, configured, or adapted to compare the weight of the items 12 in the receptacle 18 or shelf 26 before the trigger event to the weight of the items 12 in the receptacle 18 or shelf 26 after the trigger event. If the weight of the items 12 in the receptacle 18 or shelf 26 has not changed (or is within a threshold range of the weight before the trigger event), the movement sensor 102 for that receptacle 18 or shelf 26 may have been inadvertently or falsely triggered. Accordingly, the receptacle 18 or shelf 26 may not need to be scanned and a scanning time for scanning that receptacle 18 or shelf 26 may be avoided. However, if the weight of the items 12 in or on the receptacle 18 or the shelf 26 has changed (or is not within a threshold range of the weight before the trigger event), the central control device 40 may be programmed, configured, or adapted to determine that the receptacle 18 or shelf 26 is to be scanned to determine an updated inventory for that receptacle 18, shelf 26, and/or unit 10. The antenna 30 may scan the receptacle 18 or shelf 26 a predetermined time after the triggering event occurs or after a user event occurs, for example a user closes the door 74 to the receptacle 18 or shelf 26 (or unit 10) or logs out of the unit 10.

| Movement Sensor Triggered | Weight Sensor Comparison | Scan Shelf? | Output |
| --- | --- | --- | --- |
| Yes | Same weight | No | Scan not required |
| No | Same weight (Or, alternatively, may omit comparison if movement sensor not triggered.) | No | Scan not required |
| Yes | Different weight | Yes | Scan required |
| No | Different weight | Yes | Scan required (Or, alternatively, or additionally, send Alarm or Error Message) |

Accordingly, in one preferred and non-limiting embodiment or aspect, if the movement sensor 102 of a particular receptacle 18 or shelf 26 is triggered, the receptacle 18 or shelf 26 is only scanned if the weight of the receptacle 18 or shelf 26 before the triggering event is different from the weight of the receptacle 18 or shelf 26 after the triggering event. Receptacles 18 or shelves 26 for which the movement sensor 102 is not triggered may not be scanned. Unnecessary scanning time is thus avoided. The display mechanism 52 may output a message indicating whether scanning is required. In another preferred and non-limiting embodiment or aspect, if the movement sensor 102 of a particular receptacle 18 or shelf 26 is not triggered, but a weight of the receptacle 18 or shelf 26 before a triggering event, e.g., a door of receptacle 18 or shelf 26 being opened, or a user accessing or being authorized by the tracking unit 10, is different from the weight after the triggering event, the display mechanism 52 may display an error message indicating that the movement sensor 102 may not be functioning correctly (or an alarm may be transmitted to a user), and the receptacle 18 or shelf 26 should be scanned. The error message or alarm may be sent wirelessly (e.g., in the form of a text, an email, and/or the like) to a user, administrative person, maintenance worker, and/or the like. In response, it can be determined whether the movement sensor 102 has become inoperable or requires maintenance, or the weight sensor 104 has incorrectly indicated a weight change. In addition, if a weight change was indicated, but the scan results indicate that no objects or items have been added to or removed from the receptacle 18 or shelf 26, a similar alarm or error message may be displayed or transmitted to indicate a problem with the weight sensor 104.

Although a preferred and non-limiting embodiment or aspect is disclosed as providing a movement sensor 102 and a weight sensor 104 for each receptacle 18 or shelf 26, preferred embodiment or aspects are not limited thereto, and an item storage and tracking unit 10 may include only a movement sensor 102 for each receptacle 18 or shelf 26, or only a weight sensor 104 for each receptacle 18 or shelf 26. If the item storage and tracking unit 10 includes only the movement sensor 102, receptacles 18 or shelves 26 corresponding to movement sensors 102 that register triggering events are scanned in response to the trigger event, whereas receptacles 18 or shelves 26 corresponding to movement sensors 102 that do not register a triggering event are not scanned. If the item storage and tracking unit 10 includes only the weight sensors 104, receptacles 18 or shelves 26 corresponding to weight sensors 104 measuring a weight of the items 12 on the receptacle 18 or shelf 26 before a user access event, e.g., a door 74 to the housing 16 opening or a user authentication, that is different (or beyond a threshold) than a weight of the items 12 on the receptacle 18 or shelf 26 after the user access event, are scanned, whereas receptacles 18 or shelves 26 corresponding to weight sensors 104 measuring a weight of the items 12 on the receptacle 18 or shelf 26 before a user access event that is the same (or within a threshold) as a weight of the items 12 on the receptacle 18 or shelf 26 after the user access event are not scanned.

The item storage and tracking unit 10 may include a single door 74 providing access to each receptacle 18 or shelf 26, multiple doors 74, each individually providing access to a single receptacle 18 or shelf 26, or any combination thereof. Alternatively, the item storage and tracking unit 10 may not include any door 74, and the receptacles 18 or shelves 26 may be open to an exterior of the item storage and tracking unit 10. A preferred and non-limiting embodiment or aspect of an item storage and tracking unit 10 may include one or more open receptacles 18 or shelves 26, for example, as shown in FIG. 4. The central control device 40 may register an opening or closing (or movement) of the door 74 as a user event indicating that a user has accessed the item storage and tracking unit 10, and control a scanning time of the antenna 30 of each receptacle 18 or shelf 26 based at least partly on the detected user event.

If the item storage and tracking unit 10 includes one or more doors 74, it may include one or more lock mechanisms 62 associated with the doors 74 to the receptacles 18 or shelves 26. The lock mechanism 62 is in communication with the central control device 40 via the input/output mechanism 38 and serves to prevent access to the item storage and tracking unit 10 based upon action signals sent by the central control device 40. It is this lock mechanism 62, together with the user authorization and control system, which creates a securement system. The securement system, therefore, prevents any unauthorized access to the item storage and tracking unit 10. It is also envisioned that a physical master key is provided and capable of allowing authorized access to the item storage and tracking unit 10 during a power outage or other emergency situation. However, other preferred and non-limiting embodiment or aspects need not include a lock mechanism 62 or a door 74 to the receptacle 18 or shelf 26.

In one preferred and non-limiting embodiment or aspect, the signal emitting device 14, in the form of an RF/ID transponder 28, may be a tag or label affixed to each item 12. As discussed above, this tag or label may emit a unique signal corresponding to the identity of the specific item 12 or type or category of item 12. In order to provide initial input to the central control device 40 of the identity of item 12, the input mechanism 56 may include a recognition signal receiver 66 in communication with the central control device 40. This recognition signal receiver 66 may receive initial input signals corresponding to the identity of the items 12 or category of items 12. As seen in FIG. 2A, and in another embodiment or aspect, the recognition signal receiver 66 is an antenna 30 located on the item storage and tracking unit 10. This antenna 30 may serve two purposes. First, this antenna 30 increases utility administration. As the RF/ID transponder 28 is affixed to an item 12, the RF/ID transponder 28 is read and its unique identification must be associated with that particular item 12. This enables the item 12 to be identified later when the RF/ID transponder 28 is scanned or read in the receptacle 18 or shelf 26.

The second purpose of this antenna 30 is to allow selective access to the item storage and tracking unit 10, and its receptacles 18 or shelves 26, as part of the securement system. Depending upon the configuration of the item storage and tracking unit 10, a user may have an identification badge, also affixed with an RF/ID tag, which they may wave over the antenna 30, the recognition signal receiver 66, and/or the input mechanism 56. As a unique identification of the RF/ID tag is read, the central control device 40 identifies the tag user with a list of those who have access to the item storage and tracking unit 10 (and/or the specific receptacles 18 or shelves 26 therein). If there is a match, the central control device 40 sends a signal to the lock mechanism 62 via the input/output mechanism 38 in a relay to unlock the doors 74 of all of the receptacles 18 or shelves 26, or a door 74 of only a specific receptacle 18 or shelf 26.

For example, alternatively, or in addition to performing scanning in response to the movement sensor 102 and/or the weight sensor 104, the receptacles 18 or shelves 26 that are associated with the RF/ID tag, i.e., those receptacles 18 or shelves 26 that the user holding the RF/ID tag is authorized to access, may be automatically scanned in response to the user accessing the tracking unit 10 with the RF/ID tag. Alternatively, the user may use the RF/ID tag to access a specific receptacle 18 or shelf 26 via its associated antenna(s) 30, and only the specific receptacle 18 or shelf 26 which detected the user's RF/ID tag is scanned. That is, the control device 24 may control only the particular antennae 30 associated with that receptacle 18 or shelf 26, whose antenna 30 detected the RF/ID tag, to scan the receptacle 18 or shelf 26 after access to the receptacle 18 or shelf 26 (or the unit 10) has ended, and the other antennae 30 for the other receptacles 18 or shelves 26 may remain inactive. Accordingly, access to a particular receptacle 18 or shelf 26 may be determined based solely on that receptacle's 18 or shelf's 26 antenna 30 detecting the presence of a user's RF/ID tag, without the use of a movement sensor 102 and/or a weight sensor 104.

In one preferred and non-limiting embodiment or aspect, all of the display mechanism 52, input mechanism 56, central control device 40, input/output mechanism 38, signal reader mechanism 36, multiplexor mechanism 34, and power control module 42 are housed within the item storage and tracking unit 10 and, in a preferred embodiment or aspect, in a top slidable shelf 26. This enables a user access to the components for programming, repair, and maintenance.

The item storage and tracking unit 10 may also include an associated computing device 68 associated, integrated, or in direct or indirect communication with the controller 24 (or central control device 40), or in place of the central control device 40. In addition, the computing device 68 may have a computing device input mechanism 70 for providing data input into the computing device 68. The computing device 68 enables a user or administrator to interact with software on the computing device 68 for controlling the item storage and tracking unit 10, or directly or indirectly with the controller 24 (or central control device 40) in the receptacle 18 or shelf 26 of the item storage and tracking unit 10. Further, the computing device 68 may have functionality, such that it can program, modify, maintain, and otherwise interact with or control the controller 24 (or central control device 40) in the item storage and tracking unit 10. Further, in order to provide easy movement of a specific item storage and tracking unit 10 to a different area in a building, the item storage and tracking unit 10 may have wheels 72 attached to the housing 16 for easy movement.

The present invention is particularly useful in the field of medicine, and, in particular, at hospitals. In a hospital application, the items 12 are typically medical items, such as containers of medicine, medical devices, medical components, instruments, and/or the like. A specific example of the use of the item storage and tracking unit 10 in connection with a hospital follows.

Items 12 are received from a distributor or manufacturer at the hospital's central supply room, optionally with the RF/ID transponder 28, in the form of a tag or label, already affixed to the item 12, using a set tag-to-item association scheme. If the item 12 arrives with no RF/ID transponder 28 attached, hospital employees can affix the RF/ID transponder 28 themselves, and perform the tag-to-item association using the input mechanism 56 or recognition signal receiver 66 located on the housing 16. If the unit 10 includes a locking mechanism 62, the employee then waves his or her RF/ID badge over the input mechanism 56 or recognition signal receiver 66, thereby causing doors of the receptacles 18 or shelves 26 of the item storage and tracking unit 10 to open. The items 12 are then placed inside the receptacles 18 or shelves 26 and closed. As soon as the receptacles 18 or shelves 26 (or the door providing access thereto) are closed, the controller 24 (or central control device 40) performs a comparison between the inventories of the accessed and/or impacted receptacles 18 or shelves 26 (as determined by the movement sensors 102 and/or weight sensors 104) before and after they are opened to determine the added items 12, and who placed what items 12 inside. The inventory process may be implemented and performed automatically by the controller 24 (or central control device 40).

During operational use, nurses or clinicians wave their RF/ID badge over the input mechanism 56 or recognition signal receiver 66, thereby unlocking the item storage and tracking unit 10. They may access (e.g., slide a drawer or open a door) to the receptacles 18 or shelves 26 to which they have authorized access and take whatever items 12 they need. There is no need for nurses or clinicians to keypunch an access code or press a button to indicate that they have taken an item 12. As soon as the drawer is shut or the doors to the receptacles 18 or shelves 26 are closed, items 12 removed from the accessed or impacted receptacles 18 or shelves 26 (as determined by the movement sensors 102 and/or the weight sensors 104) are automatically associated with the person who just accessed the receptacles 18 or shelves 26. The controller 24 (or central control device 40) then subtracts the item 12 from the inventory, or, if an item 12 was added, adds the item 12 to the inventory. Only the receptacles 18 or shelves 26 that are accessed or impacted by the person, i.e., the receptacles 18 or shelves 26 for which the movement sensor 102 was triggered and/or the weight sensor 104 detected a weight change, are scanned. Alternatively, and as discussed, only the receptacles 18 or shelves 26 to which the person has authorization to access may be scanned. Accordingly, the next nurse or clinician needing to access the unit 10 has a reduced waiting time while the unit 10 updates its inventory.

During idle periods, the controller 24 (or central control device 40) performs inventories at set intervals. If a particular item 12 inventory is below a set par (or minimum) level, the controller 24 (or central control device 40) may send a message to the hospital's billing and purchasing system to purchase more of that particular item 12 over the network 48.

In this manner, the present invention provides an item storage and tracking unit 10, such as a cabinet, utilizing RF/ID technology to dispense supplies with security and accountability, without the need for any data entry and with reduced scanning time. The present invention has many advantages over existing devices and methods for controlling inventory including a reduced scanning time while maintaining scanning accuracy, avoiding unnecessary scanning time, and, optionally, more reliable shielding between receptacles 18 or shelves 26.

Although the invention has been described in detail for the purpose of illustration based on what is currently considered to be the most practical and preferred embodiment or aspects, it is to be understood that such detail is solely for that purpose and that the invention is not limited to the disclosed embodiment or aspects, but, on the contrary, is intended to cover modifications and equivalent arrangements that are within the spirit and scope of the appended claims. For example, it is to be understood that the present invention contemplates that, to the extent possible, one or more features of any embodiment or aspect can be combined with one or more features of any other embodiment or aspect.

What is claimed is:

1. An item storage and tracking unit for holding a plurality of discrete items, comprising:
   a housing including a plurality of receptacles positioned therein and defining a plurality of associated inner areas;
   at least one signal emitting device associated with at least one item of the plurality of discrete items and configured to emit a signal, wherein the at least one item is accessible by accessing at least one receptacle of the plurality of receptacles;
   at least one movement sensor associated with each receptacle of the plurality of receptacles and configured to detect access to the at least one receptacle;
   at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to the at least one movement sensor associated with the associated receptacle detecting access to the associated receptacle; and
   at least one weight sensor associated with each receptacle of the plurality of receptacles and configured to measure a weight before the at least one movement sensor associated with the associated receptacle detects an access to the associated receptacle, and a weight after the at least one movement sensor associated with the associated receptacle detects an access to the associated receptacle, wherein the at least one signal receiving arrangement is configured to not initiate a scan of the inner area of the associated receptacle if the weight before the detected access is substantially equal to the weight after the detected access.

2. The item storage and tracking unit according to claim 1, wherein the signal comprises a characteristic unique to the at least one item and/or a type of item.

3. The item storage and tracking unit according to claim 1, wherein at least one of the plurality of items is positionable within at least one of the inner areas in any position and/or orientation.

4. The item storage and tracking unit according to claim 1, wherein the at least one signal emitting device comprises at least one radio frequency transponder, and the at least one signal receiving arrangement comprises at least one antenna.

5. The item storage and tracking unit according to claim 1, wherein the at least one signal receiving arrangement is configured to not initiate a scan of the inner area of the associated receptacle for the signal emitted from the at least one signal emitting device if the at least one movement sensor associated with the associated receptacle does not detect access to the associated receptacle.

6. The item storage and tracking unit according to claim 1, wherein the at least one signal receiving arrangement is configured to scan the inner area of the associated receptacle if the weight before the detected access is different from the weight after the detected access.

7. The item storage and tracking unit according to claim 1, wherein at least one surface or area of the unit comprises at least one shielding element configured to at least one of minimize, redirect, and prevent the signal emitted from the at least one signal emitting device from passing therethrough.

8. The item storage and tracking unit according to claim 7, further comprising at least one absorption layer between the at least one signal receiving arrangement and the at least one shielding element.

9. The item storage and tracking unit of claim 8, wherein the at least one weight sensor is attached to a bottom side of the at least one shielding element opposite the at least one absorption layer.

10. A method of determining an inventory of an item storage and tracking unit holding a plurality of discrete items, comprising:
(a) providing the item storage and tracking unit, comprising:
a housing including a plurality of receptacles positioned therein and defining a plurality of associated inner areas,
at least one signal emitting device associated with at least one item of the plurality of discrete items and configured to emit a signal, wherein the at least one item is accessible by accessing at least one receptacle of the plurality of receptacles,
at least one movement sensor associated with each receptacle of the plurality of receptacles and configured to detect access to the associated receptacle,
at least one weight sensor associated with each receptacle of the plurality of receptacles and configured to measure a weight before the at least one movement sensor associated with the associated receptacle detects an access to the associated receptacle, and a weight after the at least one movement sensor associated with the associated receptacle detects an access to the associated receptacle,
at least one signal receiving arrangement associated with each receptacle of the plurality of receptacles; and
(b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to the at least one movement sensor associated with the associated receptacle detecting access to the associated receptacle, and wherein the scan is not initiated if the weight before the detected access is substantially equal to the weight after the detected access.

11. An item storage and tracking unit for holding a plurality of discrete items, comprising:
a housing including a plurality of receptacles positioned therein and defining a plurality of associated inner areas;
at least one signal emitting device associated with at least one item of the plurality of discrete items and configured to emit a signal, wherein the at least one item is accessible by accessing at least one receptacle of the plurality of receptacles;
at least one weight sensor associated with each receptacle of the plurality of receptacles and configured to measure a weight before an access to the item storage and tracking unit is performed by a user and a weight after an access to the item storage and tracking unit is performed by the user; and
at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to a comparison of the weight before the user access to the weight after the user access, and wherein the at least one weight sensor of the associated receptacle comprises at least one platform connected by at least one cable to the weight sensor.

12. The item storage and tracking unit according to claim 11, wherein at least one of the plurality of items is positionable within at least one of the inner areas in any position and/or orientation.

13. The item storage and tracking unit according to claim 11, further comprising at least one movement sensor associated with each receptacle of the plurality of receptacles and configured to detect access to at least one receptacle of the plurality of receptacles.

14. The item storage and tracking unit according to claim 13, wherein the at least one signal receiving arrangement is configured to not initiate a scan of the inner area of the associated receptacle if the at least one movement sensor does not detect access.

15. The item storage and tracking unit according to claim 11, wherein the access is detected by the sensing of at least one of the opening a door of the unit and the opening a drawer of the unit.

16. A method of determining an inventory of an item storage and tracking unit holding a plurality of discrete items, comprising:
(a) providing the item storage and tracking unit comprising:
a housing including a plurality of receptacles positioned therein and defining a plurality of associated inner areas,
at least one signal emitting device associated with at least one item of the plurality of discrete items and configured to emit a signal, wherein the at least one item is accessible by accessing at least one receptacle of the plurality of receptacles,
at least one weight sensor associated with each receptacle of the plurality of receptacles and configured to detect weight change in or associated with the associated receptacle, and
at least one signal receiving arrangement associated with each receptacle of the plurality of receptacles; and
(b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to a comparison of the weight before the user access to the weight after the user access, and wherein the at least one weight sensor of the associated receptacle comprises at least one platform connected by at least one cable to the weight sensor.

17. An item storage and tracking unit for holding a plurality of discrete items, comprising:
a housing including a plurality of receptacles positioned therein and defining a plurality of associated inner areas;

at least one signal emitting device associated with at least one item of the plurality of discrete items and configured to emit a signal, wherein the at least one item is accessible by accessing at least one receptacle of the plurality of receptacles; and at least one signal receiving arrangement associated with each receptacle of the plurality of receptacles and configured to scan at least a portion of the inner area of the associated receptacle for the signal emitted from the at least one signal emitting device associated with the at least one item of the plurality of discrete items, wherein the scan is initiated at least partly in response to at least one user signal emitting device associated with at least one user being detected by the at least one signal receiving arrangement of the associated receptacle, wherein the at least one user signal emitting device associated with the at least one user is configured to emit a signal that comprises a characteristic unique to the at least one user, and wherein the at least one signal receiving arrangement of the associated receptacle detects the signal emitted from the at least one user signal emitting device that comprises the characteristic unique to the at least one user.

18. A method of determining an inventory of an item storage and tracking unit holding a plurality of discrete items, comprising:

(a) providing the item storage and tracking unit comprising:
a housing including a plurality of receptacles positioned therein and defining a plurality of associated inner areas,
at least one signal emitting device associated with at least one item of the plurality of discrete items and configured to emit a signal, wherein the at least one item is accessible by accessing at least one receptacle of the plurality of receptacles,
at least one signal receiving arrangement associated with each receptacle of the plurality of receptacles; and (b) scanning, by the at least one signal receiving arrangement, at least a portion of the inner area of the associated receptacle for the signal emitted from the at least one signal emitting device associated with the at least one item of the plurality of discrete items, wherein the scan is initiated at least partly in response to at least one user signal emitting device associated with at least one user being detected by the at least one signal receiving arrangement of the associated receptacle, wherein the at least one user signal emitting device associated with the at least one user is configured to emit a signal that comprises a characteristic unique to the at least one user and wherein the at least one signal receiving arrangement of the associated receptacle detects the signal emitted from the at least one user signal emitting device that comprises the characteristic unique to the at least one user.

\* \* \* \* \*